United States Patent

Thundat

Patent Number: 6,016,686
Date of Patent: Jan. 25, 2000

[54] MICROMECHANICAL POTENTIOMETRIC SENSORS

[75] Inventor: Thomas G. Thundat, Knoxville, Tenn.

[73] Assignee: Lockheed Martin Energy Research Corporation, Oak Ridge, Tenn.

[21] Appl. No.: 09/042,601

[22] Filed: Mar. 16, 1998

[51] Int. Cl.[7] .................................................. G01N 27/00
[52] U.S. Cl. ...................... 73/23.2; 73/24.06; 422/52.01; 422/83; 436/163
[58] Field of Search .................................. 73/24.06, 23.2, 73/53.01, 61.41; 422/82.01, 68.1, 83; 436/163

[56] References Cited

U.S. PATENT DOCUMENTS

| | | |
|---|---|---|
| Re. 35,544 | 7/1997 | Snow . |
| 4,236,893 | 12/1980 | Rice . |
| 4,242,096 | 12/1980 | Oliveira et al. . |
| 4,596,697 | 6/1986 | Ballato . |
| 4,637,987 | 1/1987 | Minten et al. . |
| 4,735,906 | 4/1988 | Bastiaans . |
| 4,847,193 | 7/1989 | Richards et al. . |
| 4,905,701 | 3/1990 | Cornelius . |
| 4,906,840 | 3/1990 | Zdeblick et al. . |
| 4,999,284 | 3/1991 | Ward et al. . |
| 5,001,053 | 3/1991 | Takahashi et al. . |
| 5,130,257 | 7/1992 | Baer et al. . |
| 5,135,852 | 8/1992 | Ebersole et al. . |
| 5,156,972 | 10/1992 | Issachar . |
| 5,179,028 | 1/1993 | Vali et al. . |
| 5,221,415 | 6/1993 | Albrecht et al. . |
| 5,283,037 | 2/1994 | Baer et al. . |
| 5,306,644 | 4/1994 | Myerholtz et al. . |
| 5,323,636 | 6/1994 | McGowan et al. . |
| 5,339,675 | 8/1994 | DiLeo et al. . |
| 5,363,697 | 11/1994 | Nakagawa . |
| 5,372,930 | 12/1994 | Colton et al. . |
| 5,411,709 | 5/1995 | Furuki et al. . |
| 5,445,008 | 8/1995 | Wachter et al. .......................... 73/24.06 |
| 5,445,970 | 8/1995 | Rohr . |
| 5,445,971 | 8/1995 | Rohr . |

(List continued on next page.)

OTHER PUBLICATIONS

*MEMS Sensors and Wireless Telemetry for Distributed Systems*—C. L. Britton et al., presented at the SPIE 5th International Symposium on Smart Materials and Structures, Mar. 2, 1998, San Diego, California.

*Microfabrication of Cantilever Styli for the Atomic Force Microscope*—T. R. Albrecht, 1990 American Vacuum Society, pp. 3386–3396, v.

*Photothermal Spectroscopy with Femtojoule Sensitivity Using a Micromechanical Device*—J. R. Barnes, et al., Nature, vol. 372 –Nov. 3, 1994, pp. 79–81.

(List continued on next page.)

*Primary Examiner*—Michael Brock
*Attorney, Agent, or Firm*—Nexsen Pruet Jacobs & Pollard, LLP

[57] ABSTRACT

A microcantilever potentiometric sensor utilized for detecting and measuring physical and chemical parameters in a sample of media is described. The microcantilevered spring element includes at least one chemical coating on a coated region, that accumulates a surface charge in response to hydrogen ions, redox potential, or ion concentrations in a sample of the media being monitored. The accumulation of surface charge on one surface of the microcantilever, with a differing surface charge on an opposing surface, creates a mechanical stress and a deflection of the spring element. One of a multitude of deflection detection methods may include the use of a laser light source focused on the microcantilever, with a photo-sensitive detector receiving reflected laser impulses. The microcantilevered spring element is approximately 1 to 100 $\mu$m long, approximately 1 to 50 $\mu$m wide, and approximately 0.3 to 3.0 $\mu$m thick. An accuracy of detection of deflections of the cantilever is provided in the range of 0.01 nanometers of deflection. The microcantilever apparatus and a method of detection of parameters require only microliters of a sample to be placed on, or near the spring element surface. The method is extremely sensitive to the detection of the parameters to be measured.

32 Claims, 7 Drawing Sheets

U.S. PATENT DOCUMENTS

| | | |
|---|---|---|
| 5,477,716 | 12/1995 | Snow . |
| 5,482,678 | 1/1996 | Sittler . |
| 5,494,639 | 2/1996 | Grzegorzewski . |
| 5,501,986 | 3/1996 | Ward et al. . |
| 5,552,274 | 9/1996 | Oyama et al. . |
| 5,563,341 | 10/1996 | Fenner et al. ........................ 73/335.11 |
| 5,595,908 | 1/1997 | Fawcett et al. . |
| 5,658,732 | 8/1997 | Ebersole et al. . |
| 5,705,399 | 1/1998 | Larue . |
| 5,719,324 | 2/1998 | Thundat et al. . |
| 5,807,758 | 9/1998 | Lee et al. ............................... 436/526 |

OTHER PUBLICATIONS

*A Mechanical Nanosensor in the Gigahertz Range: Where Mechanics Meets Electronics*—Surface Science Letters–1994.

*A Nondestructive Method for Determining the Spring Constant of Cantilevers for Scanning Force Microscopy*—J. P. Cleveland et al., Science, vol. 64, No. 2, Feb. 1993.

*Observation of a Chemical Reaction Using a Micromechanical Sensor*—J. K. Gimzewski et al., Chemical Physics Letters, vol. 217, No. 5.6, pp. 589–594.

*Measuring Intermolecular Binding Forces with the Atomic–Force Microscope: The Magnetic Jump Method*—Hoh et al., Proceedings, Fifty–Second Annual Meeting Microscopy Society of America, Jul. 31 –Sep. 5, 1994, pp. 1054–1055.

*Journal of the American Chemical Society*—B. G. Rao et al., Jun. 3, 1992, vol. 114, No. 12.

*Sensing Discrete Steptavidin–Biotin Interactions with Atomic Force Microscopy*—Gil U. Lee, et al., Langmuir, vol. 10, No. 2, 1994.

MICROMECHANICAL POTENTIOMETRIC SENSORS

CROSS-REFERENCE TO RELATED APPLICATIONS

The invention relates to the following patents, Wachter et al., U.S. Pat. No. 5,445,008, issued Aug. 29, 1995, and Thundat et al., U.S. Pat. No. 5,719,324, issued Feb. 17, 1998, which are herein incorporated by reference.

STATEMENT AS TO RIGHTS TO INVENTIONS MADE UNDER FEDERALLY-SPONSORED RESEARCH AND DEVELOPMENT

The United States Government has certain rights in this invention pursuant to contracts numbers DE-AC05-96OR22464 and DE-AC05-84OR21400, between the U.S. Department of Energy and Lockheed Martin Energy Research Corporation.

BRIEF SUMMARY OF THE INVENTION

The invention relates generally to technology for detecting chemical and physical parameters in a media, and more particularly to utilizing microcantilevers to detect hydrogen ion and specific ion concentrations, and redox potential in a media.

BACKGROUND OF THE INVENTION

Potentiometric measurements are commonly utilized in chemical, biophysical and biochemical studies to determine hydrogen ion concentrations (pH), specific ion concentrations, and measurements of redox potentials in a media that may, or does contain biological material. Prior techniques for measurements include using glass electrodes and redox measurements with metal electrodes. There is a great interest in miniaturizing of devices for sensitive and reliable measurements of biologically significant parameters, and in increasing the accuracy of measurements while utilizing smaller amounts of sampling media exposed to the detecting apparatus.

In Thundat et al., U.S. Pat. No. 5,719,324, a piezoelectric transducer is disclosed that is fabricated with a cantilever having a spring element treated with a chemical having an affinity for a specific vapor phase chemical. An oscillator means maintains a resonant vibrational frequency during detection of a chemical, with changes in resonant frequency indicating amounts of targeted chemical detected in the monitored atmosphere.

In Wachter et al., U.S. Pat. No. 5,445,008, a mass microsensor is disclosed that is fabricated with a microcantilever having a chemical coating, the cantilever is oscillated by a piezoelectric transducer, the chemical coating on the microcantilever absorbs a targeted chemical from the monitored atmosphere. The resonant frequency of the microcantilever is analyzed to determine changes that indicate the amount of targeted chemical that is within the monitored atmosphere.

In Marcus et al., U.S. Pat. No. 5,475,318, a microprobe is disclosed that includes a microcantilever, a base, a probe tip projecting from the base, and a heating element that heats the probe tip, which comes into contact with a material to be investigated.

In Hafeman, U.S. Pat. No. 4,963,815, a device and method is provided for determining an analyte by measuring a redox potential-modulated photoinducing electrical signal from an electronically conducting layer on a semiconductor device.

In Kolesar, U.S. Pat. No. 4,549,427, a chemical nerve agent detector is disclosed that includes a transducer having two microcantilever oscillators. The active of two microcantilevers have a chemically selective substance that absorbs chemical nerve agents from the atmosphere, with modifications in the oscillation of the active microcantilever, and comparisons allowed between the frequency of the active cantilever and the reference cantilever.

The prior art obtained pH measurements with glass electrodes and redox measurements are accomplished with metal electrodes. Both of these techniques involve measuring very small potential changes and require high input impedance devices. One device utilized is the chemically sensitive field effect transistor in which the gate region of a transistor is made sensitive to chemical events through their effect on the gate potential. A similar device called a light addressable potentiometric semiconductor sensor has been utilized for biochemical process sensing by detecting potentiometric sensing through changes in pH, redox potential, or transmembrane potential. All of the above described methods and devices utilize electrical means for potentiometric sensing for detection and measuring of biologically significant parameters such as pH, redox potential, and ion concentrations of selective ions with limited sensitivities in relatively large sample volumes. Miniaturization is difficult using the prior art methods and devices. Thus there exists room for improvement within the art.

SUMMARY OF THE INVENTION

It is an object of this invention to provide a detection and measuring method for potentiometric measuring of chemical, biophysical, and biochemical parameters within a sample of monitored media.

It is a further object of this invention to provide a microcantilevered spring element with coatings having an affinity for hydrogen ion concentrations within a sample of monitored media.

It is an additional object of this invention to provide a microcantilevered spring element with coatings that respond to the rate of changes in pH within a sample of a monitored media.

It is a further additional object of this invention to provide a microcantilevered spring element with coatings that respond to redox potential and selected ion concentrations of components in a sample of a monitored media.

It is a further and more particular object of this invention to provide a microcantilevered spring element that provides extremely high sensitivity, miniaturized size, and low power requirements.

These and other objects of the invention are accomplished by an apparatus and a method for detecting and measuring physical and chemical parameters in a sample of a monitored media, including: a transducer base, at least one cantilevered spring element secured to the base, at least one surface on said spring element having a coated region with a chemical attached that accumulates a surface charge in response to the parameters in the sample of media being monitored. The spring element comprises a microcantilever that bends in response to mechanical stresses created by the surface charge density differences between the chemical coating on one surface and a relatively inert opposing surface of the microcantilever. The microcantilever is significantly small in size to allow sensitivities in the nanometer range for bending of the microcantilever, and to require only small volumes of media to measure and detect hydrogen ion and specific ion concentrations, and redox potentials within a sample of the monitored media.

Thus, the objects of the invention are accomplished by the apparatus and a method for detecting and measuring chemical and physical parameters within a sample of media as described herein.

BRIEF DESCRIPTION OF THE DRAWINGS

The invention's features and advantage will become apparent from a reading of the following detailed description, given with reference to the various figure of drawing, in which.

DETAILED DESCRIPTION OF THE PREFERRED EMBODIMENT

In accordance with this invention, it has been found that a detection method and apparatus is needed that is ultra miniaturized and is extremely sensitive to slight changes in physical, biophysical, chemical, and biochemical parameters in a media containing a wide variety of analytes including living organisms. Potentiometric measurements are commonly used in chemical, biophysical and biochemical studies. The invention described herein is capable of detecting and measuring changes in hydrogen ion concentrations, redox potential, and/or selective ion concentrations within a monitored media, including accurate measurement of the biological activity of living organisms within the media. The invention utilizes microcantilevers with at least one material coated on one surface. The opposing surface is relatively inert in comparison with the material coated surface. The coating material of one embodiment accumulates surface charge in direct proportion to the physical and chemical parameters within the media. As the surface charge density increases on one side of the microcantilever, a deflection of the microcantilever occurs in proportion to the parameter measured within the media.

Figure 1:
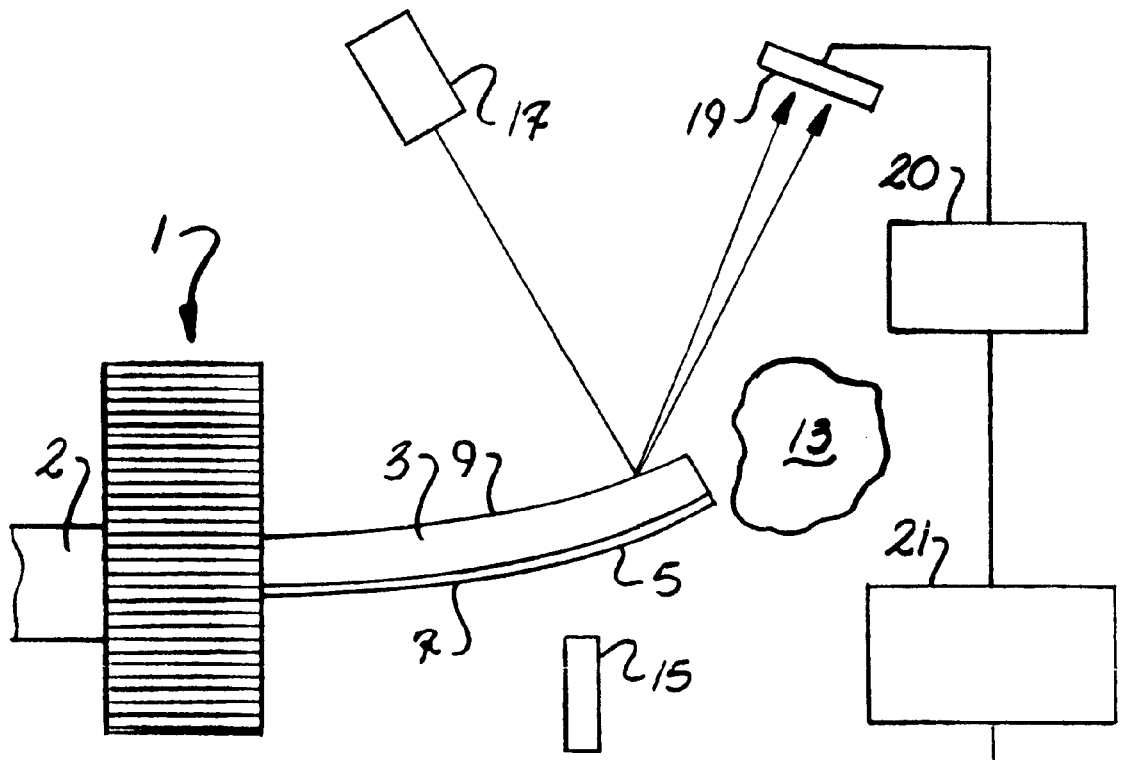
FIG. 1 is an elevational view of one alternate embodiment of the present invention.
Figure 2:
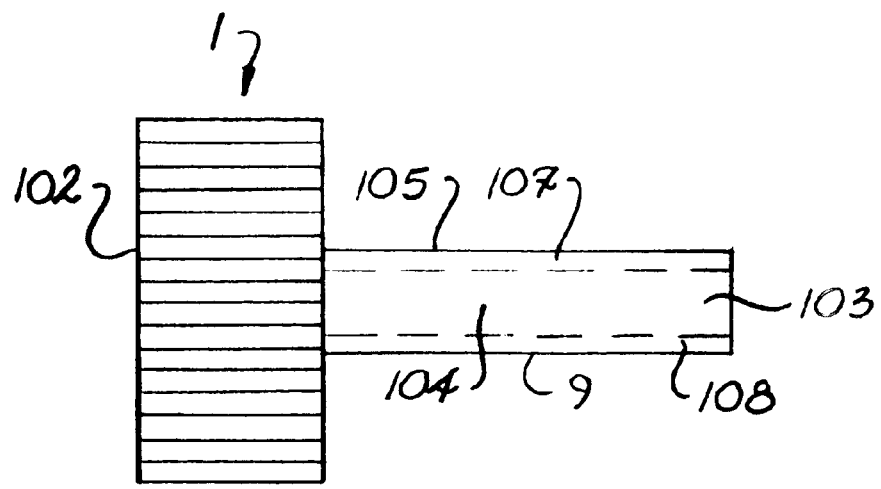
FIG. 2 is a cross-sectional side view of one alternate embodiment of the microcantilever of the present invention in a neutral position with two coatings on opposing surfaces.

In accordance with FIGS. 1 and 2, a micro-detection poteniometric apparatus 1 has a transducer base 2 having at least one sensing microcantilevered spring element (microcantilever) 3 attached. The microcantilever 3 is composed of a base material that has a coating of sensing material 7 treated on all, or a region, of a first surface 5. The coating is a first sensing material 7 that ionizes in response to hydrogen ion concentrations within a media 13 to be sampled. As the sensing material 7 ionizes, the first surface 5 accumulates surface charge proportional to the hydrogen ion concentrations within the media 13. As surface charge accumulates on one surface 5 of the cantilever, and changes occur in the differential surface charge density across the surfaces of the cantilever 3, the resulting surface stress will deflect the cantilever (FIG. 1).

Localized variations in pH within a sample 13 of a monitored media may occur near living organisms. The sensing microcantilever 3 can detect these pH changes due to biological activity of living organisms. In addition to detecting the pH of a liquid, the invention may also be used for detecting the acidic or basic nature of a gas stream. Therefore the sample 13 on a spring element 3 may be taken from a gaseous environment, a liquid environment, and/or a semi-solid media containing living organisms.

The first material or chemical compound 7 which is attached to a coated region on a portion (FIG. 3), or all (FIG. 1) of the first surface 5, may consist of silicon nitride, tantalum pentoxide, silicon oxide, platinum oxide, iridium oxide, aluminum oxide, or a comparable polymer material that is sensitive to hydrogen ions. First material 7 ionizes in response to hydrogen ion concentrations, with a surface charge density (not shown) accumulating on first surface 5 proportional to the hydrogen ion concentrations within the sample of media 13 placed on the cantilevered spring element. The base material 4 of spring element 3 may be composed of materials such as silicon, silicon nitride, germanium, polymers, ceramics, diamond, quartz, other silicon compounds, metal compounds, gallium arsenide, germanium, germanium dioxide, and zinc oxide.

The second surface 9 of spring element 3 may be coated with an inert material, or no additional coating, or a second coating with a rate for accumulation of a surface charge different than the rate of accumulation of surface charge of the first material 7. The second coating of a chemical 8 may be composed of silicon, silicon oxide, silicon nitride, other silicon compounds, polymer compounds, biopolymer compounds, or metal compounds such as gallium arsinide. The second surface 9 should have a different composition from the first material 7, to allow a different interaction of the second surface 9 with a sample 13 of the monitored media. Ideally, the second surface 9 and any second coating 8 would be inert, or relatively inert to the parameters undergoing detection when compared with the material 7 coated on first surface 5.

Figure 3:
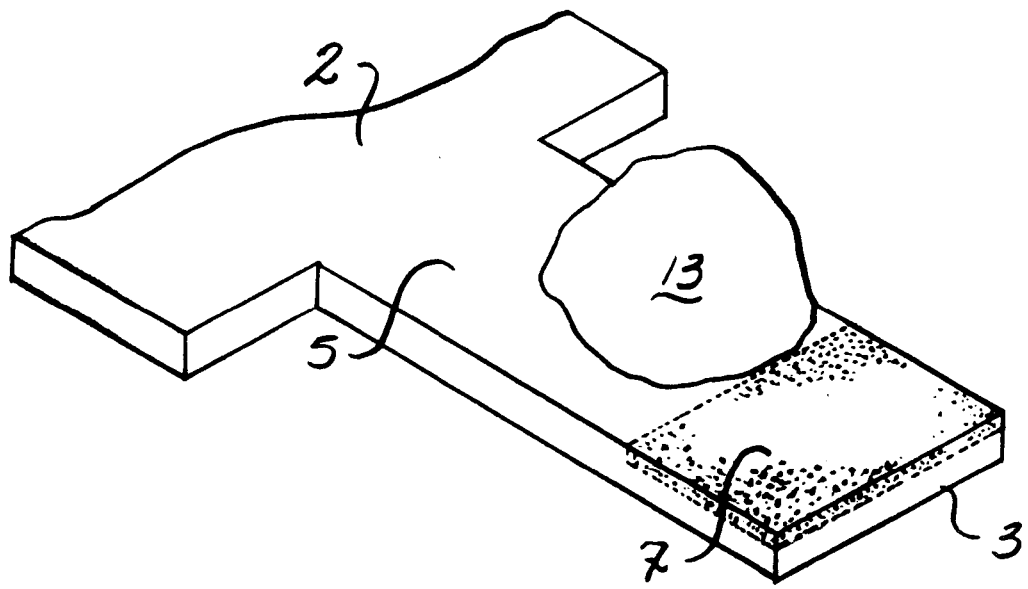
FIG. 3 is a side perspective view of one alternate embodiment of the microcantilever of the present invention in contact with the monitored media.

As depicted in FIG. 1 and FIG. 3, a sample 13 of 30 microliter or less is placed on the sensing microcantilever 3 first surface 5. The sensing material 7 develops a surface charge in relation to the pH within the sample 13, and the microcantilever 3 undergoes bending due to variations in surface charges (surface charges not shown) between the material 7 on first surface 5 and the second surface 9. As first surface 5 accumulates surface charges proportional to hydrogen ion concentrations of the sample of monitored media 13, the differential surface charge density between first surface 5 and second surface 9 creates surface stress that deflects the microcantilever 3 due to mechanical stresses created in the coated regions of spring element 3.

The typical dimensions of each microcantilevered spring element 3 are approximately 1–200 μm long, approximately 1–50 μm wide, and approximately 0.3–3 μm thick. The bending of the microcantilever 3 can be measured with a sensitivity of 0.01 nanometer (nm) by using a variety of known detection techniques such as optical beam deflection utilizing a laser beam and photodetector, or interferometric, capacitance, piezoresistance, electron tunneling, or piezo-electric detection techniques.

The sensing microcantilever 3 has a response time in the range of microseconds to milliseconds. Because the microcantilever 3 thickness is very thin, the changes in differential surface charge induced by changes in pH, specific ion concentrations, and/or redox potential are manifested as changes in differential surface stress. These changes in differential surface stress manifest themselves as changes in cantilever deflection which can be measured with a sub nanometer sensitivity. The cantilever technique offers more simplicity and higher sensitivity than the prior art. A general discussion of microcalorimetry utilizing oscillating microcantilevers is provided in Gimzewski et al. ("Observation of a chemical reaction using a micromechanical sensor," 217 *Chem. Phys. Lett.* 589, at 591–592 (1994)).

When exposed to a sample 13 of a monitored media, the charge density on the silicon nitride surface varies with changes in pH of the sample 13 of monitored media placed in contact with the sensing chemical 7. The pH dependence of the silicon nitride group is very close to Nernstian (i.e., 59 millivolt change in potential for a one unit change in pH). This pH dependent behavior is due to silanol and silamine groups on the silicon nitride surface. As a result of this differential surface charge on the cantilever, the microcantilevered spring element 3 deflection changes reproducibly with a change in pH. The deflection also changes as the pH is increased from low to high. Spring element 3 motion can be measured by laser directed light 17 onto the microcantilever 3 with deflection of the output to a photodetector 19 (position sensitive detector, (PSD)). The d.c. variation in the PSD will coincide with the bending of the microcantilever 3. Other techniques for detection of deflections of microcantilever 3 include sensing with piezoresistive, of microcantilever 3 include sensing with piezoresistive, capacitance, piezoelectric, and electron tunneling methods. Since the technique of measuring deflections described herein is sensitive to amplitudes as small as sub-nanometers, very small changes in pH can be determined.

Empirical Formulas of Analyte and Microcantilever Interaction

Silicon nitride is an excellent electrical insulator. As the pH within the sample placed on the spring element changes, surface charges collect on the surface of the silicon nitride. The presence of surface charge on one side of the spring element causes a tangential stress in the microcantilever 3. A characteristic of the present invention is that microcantilever 3 can be made to undergo bending due to changes in differential surface stress by confining the variation of surface charge density to one side of the thin microcantilever 3. Using Stoney's formula, the radius of curvature of bending of the cantilever due to absorption can be written as:

$$\frac{1}{R} = \frac{6(1-v)}{Et^2}\delta s \quad (1)$$

where R is the radius of curvature for the cantilever, v and E are Poisson's ratio and Young's modulus for the substrate respectively, t is the thickness of the cantilever and δs is the film stress. The radius of curvature due to bending of a cantilever is given by, $$\frac{1}{R} = \frac{2z}{L^2} \quad (2)$$

where z is the displacement at the unsupported end of the microcantilever and L is the length of the cantilever beam. Using (1) and (2), a relationship between the cantilever displacement and the differential surface stress in obtained:

$$z = \frac{3L^2(1-v)}{Et^2}\delta s \quad (3)$$

This bending can be measured with a sub-nanometer resolution by reflecting a light from a diode laser at the end of a cantilever into a position sensitive detector. FIG. 1 depicts the photodetector embodiment with a detection system utilizing a diode laser 17 and photodetector 19. The amount of deflection of the cantilever 3 in proportion to the differential surface charge density induced by changes in pH is analyzed by microprocessors 21 and associated computer software (not shown).

Figure 9:
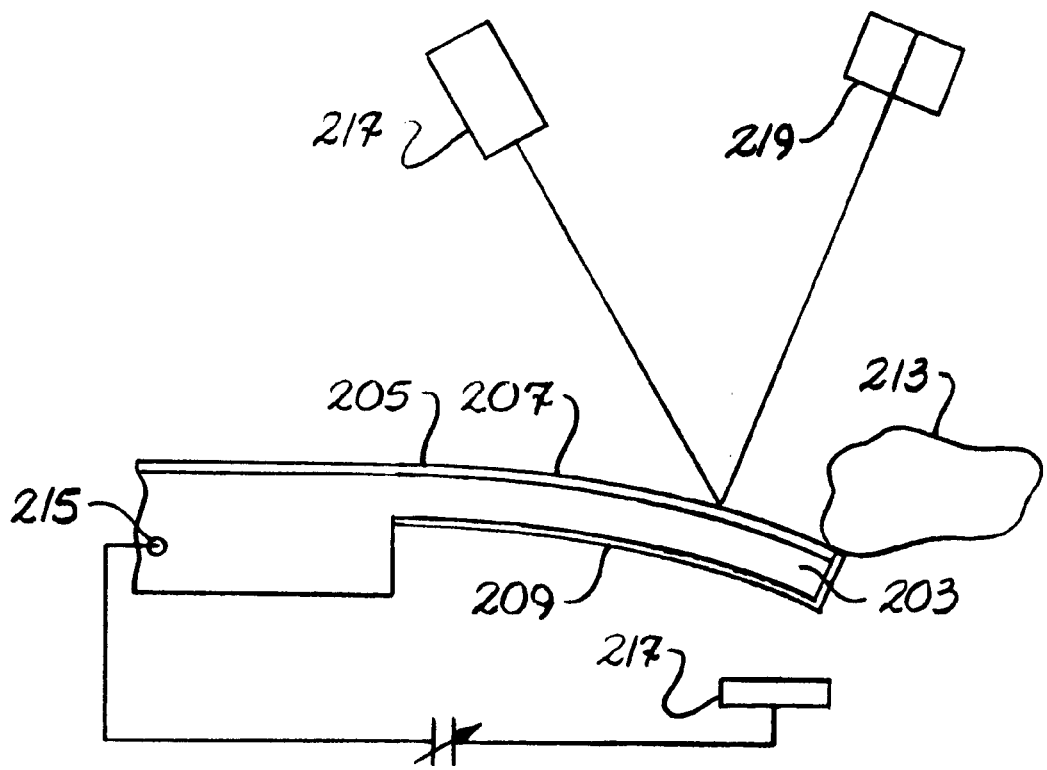
FIG. 9 is a cross-sectional side view of the microcantilever in a bent position due to a periodic applied electrical charge.
Figure 10:
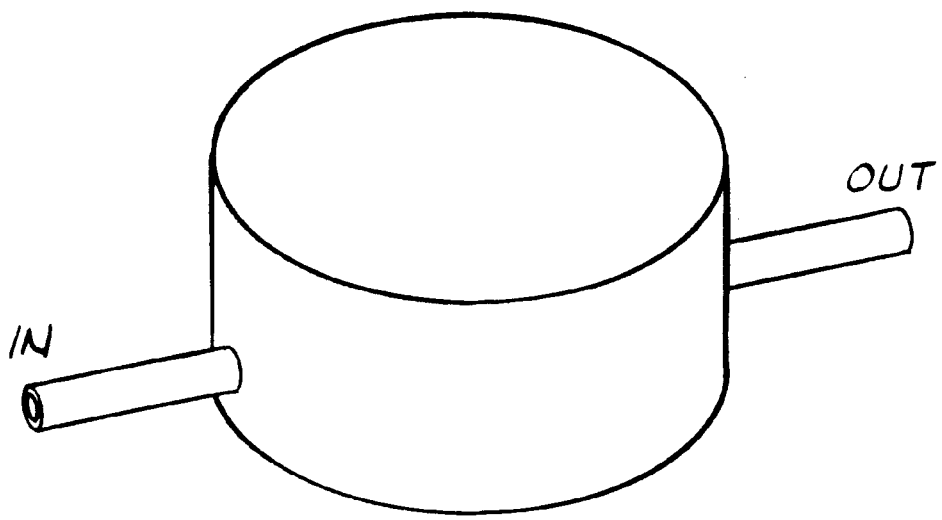
FIG. 10 is a pictorial representation of the assembled microcantilever sensor.
Figure 11:
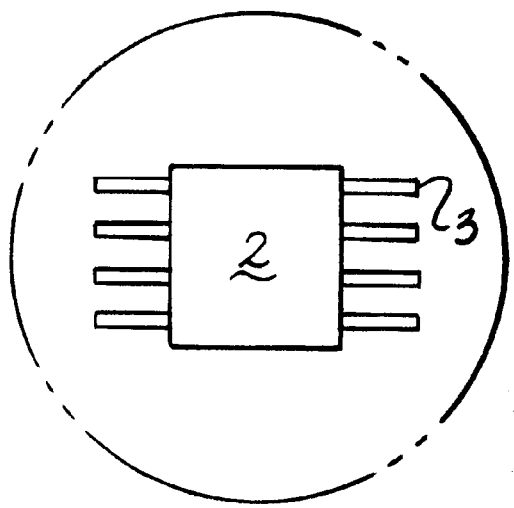
FIG. 11 is a top view of the cylindrical section of the assembled microcantilever sensor.

As an alternative variation to the above embodiment, the sensing cantilever 3 initial deflection can be adjusted by applying a known potential between the cantilever 3 and the monitored media 13. This can be achieved by a counter electrode and a reference electrode (not shown) or a controlling electrode (FIG. 9). The controlling electrode can be the reference electrode or a separate electrode (not shown). This technique is a d.c. technique which can be made into an a.c. technique by coating the inert side of the cantilever with a stress sensitive film (not shown). The bending of the cantilever can now be converted into a.c. signal by detecting the variation in resonance frequency of the cantilever. As the cantilever bends the stiffness of the cantilever changes due to stress sensitive film. The amplitude resonance frequency of the cantilever varies as the cantilever bends. Therefore, the d.c. variation in cantilever bending can be converted into an a.c. signal.

The stress-induced changes in spring constant, δκ, of the cantilever can be calculated from the bending of the cantilever.

$$\delta k = \pi^2 n \frac{(\delta s_1 - \delta s_2)}{4n_1} \quad (4)$$

where $\delta s_1$ and $\delta s_2$ are the differential stress on the cantilever surfaces and $n_1$ is a geometrical constant. The resonance frequency of the cantilever changes due to the changes in resonance frequency caused by static bending of the cantilever.

ADDITIONAL EMBODIMENTS

A second embodiment of the present invention the spring element 103 is attached to a base 102, the spring element 103 having two coating layers (FIG. 2), one layer 107 sensitive to hydrogen ions, and a second layer 108 having biomaterials in a polymer base. The biomaterial layer and/or the layer sensitive to hydrogen ions will develop a surface charge density different than the base material 104 of the cantilever 103. The second surface 105, which may be of an inert material different than the base material 104, such as ceramics, polymers, or silica. One of the layers 107 or 108 may contain enzymes, peptides, proteins, nucleic acids, carbohydrates, antibody and antigen molecules, pharmacological agents (i.e. drugs, including small organic molecules such as aspirin), and other biopolymers that interact and bind with enzymes in the sample 113 to produce pH changes on the spring elemnt surface in proportion to pH changes in the sample 113 placed on the sensing layer. Therefore the spring element 103 may be utilized for enzyme-linked immunoassays. With selection of the appropriate biopolymer, and calibration of surface charge density and associated mechanical stress buildup, the number of enzymes within a sample 113 may be calculated with the microcantilevered spring element 103.

Figure 4:
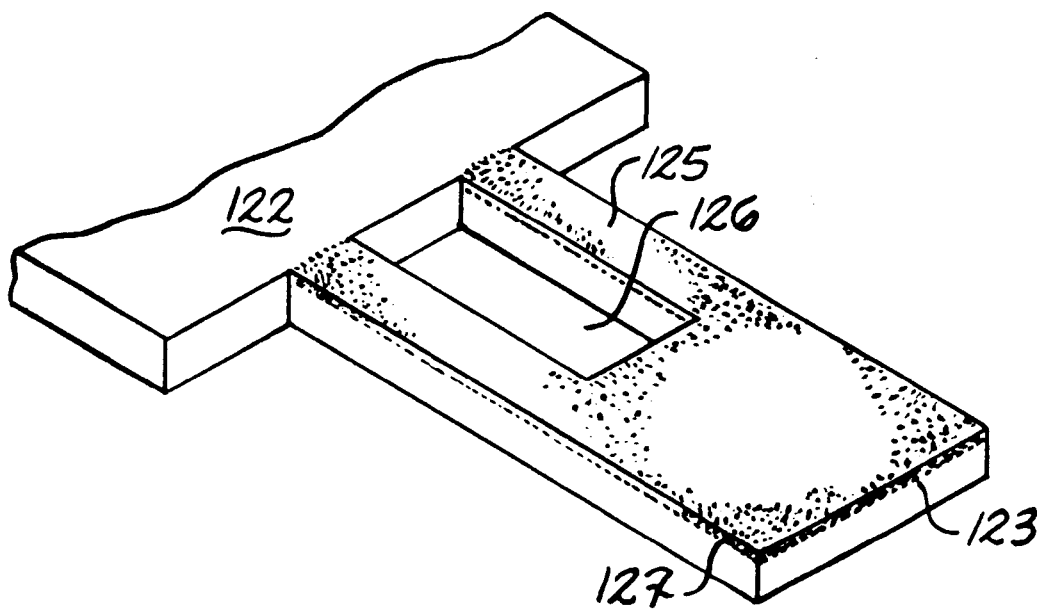
FIG. 4 is a side perspective view of another alternate embodiment of the microcantilever of the present invention.

As shown in FIG. 4, the microcantilevered spring element 123 may have a central region void 126 to form a "U" shape lever which provides additional insulation of the spring element 123 from the transducer base 122. A chemical 127 sensitive to the physical and chemical property undergoing detection is coated on one surface 125, with the spring element 123 composed of an essentially inert material.

Figure 5:
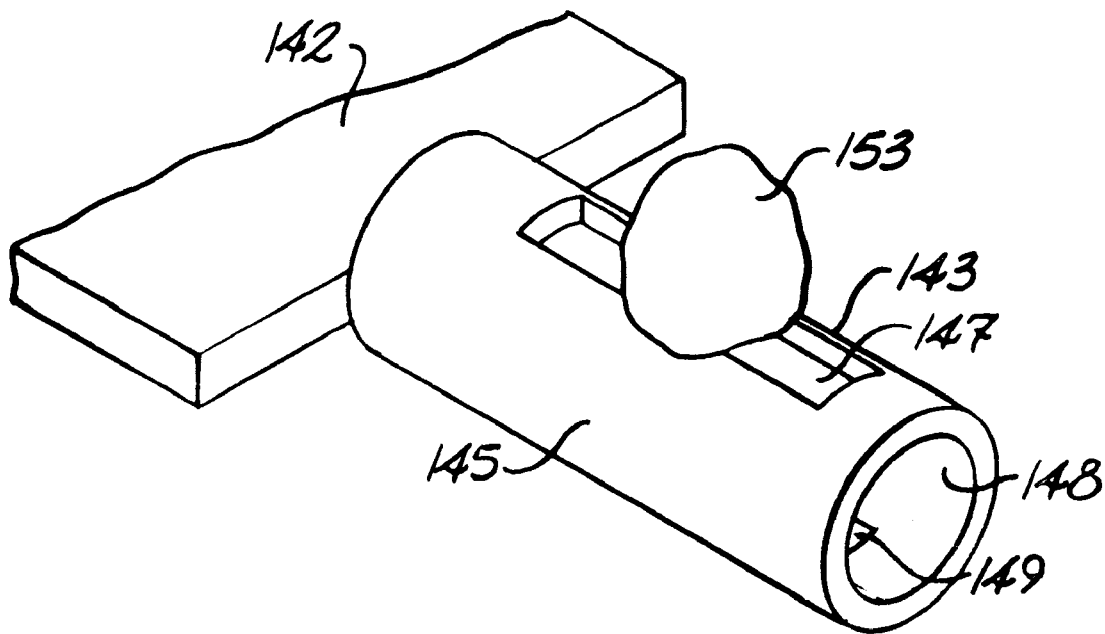
FIG. 5 is a side perspective view of another alternate embodiment of the microcantilever of the present invention in a tubular configuration.

As shown in FIG. 5, another configuration of the microcantilevered spring element includes a tubular spring element 143 that has an outer surface 145 that has a chemical 147 coating sensitive to the physical and chemical property undergoing detection. The interior surfaces 148 of the tube may have a material 149 coated on part of all of the interior surface 148 that is inert or develops surface charges at a differing rate than the outer chemical coating 147, which creates a mechanical stress in the tubular spring element 143 with resulting bending. The sample 153 of the monitored media may be placed on, or in close proximity to, chemical 147 on the spring element surface, and the sample 153 may be placed in contact with interior surfaces 148 and material 149. The tubular microcantilever may have a length of about 1 to about 200 $\mu$m, a diameter of about 1 to about 50 $\mu$m, and a wall thickness of about 0.3 to about 3.0 $\mu$m. The cylindrical microcantilever may have a length of about 1 to about 200 $\mu$m, and a diameter of about 1 to about 50 $\mu$m.

Figure 6:
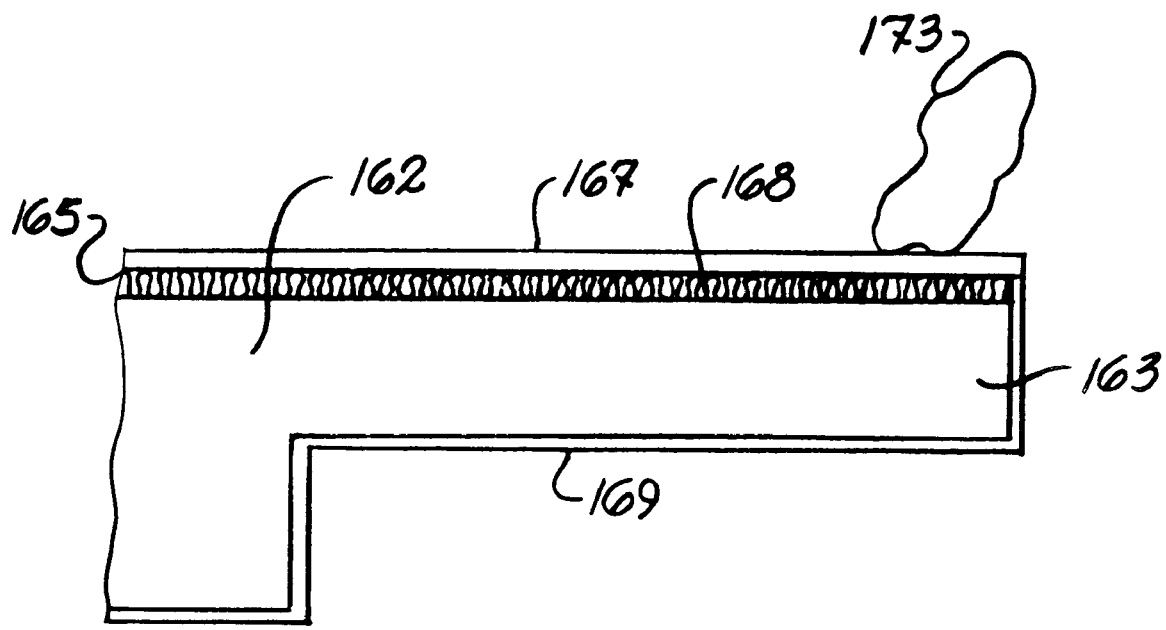
FIG. 6 is a cross-sectional side view of an alternate embodiment of the microcantilever of the present invention with an insulator and a noble metal coating.

Another detection and monitoring method utilizes the microcantilevered spring element 163 of FIG. 6 to detect the redox potential of a sample of monitored media placed on the coated regions of the spring element. As shown in FIG. 6, the spring element 163 is attached to base 162, with a first surface 165 having two coatings. The opposing surface 169 is composed of inert, or less reactive material than the first surface 165. The outer coating 167 on the first surface is composed of a noble metal such as gold or platinum in a uniform layer 167. The outer sensing surface detects the redox potential of the sample 173 placed on the outer coating 167, without interference from the properties of the base 162 or the spring element 163 due to a second layer of active insulator 168 which is a coating between the outer coating 167 and the base 162 and the spring element 163. The active insulator 168 may consist of silicon oxide, silicon nitride, aluminum oxide, iridium oxide, tantalum pentoxide and polymers sensitive to measuring redox potential. A plurality of microcantilever spring elements having a set of at least one spring element 3, 103 having one or more coatings 7, 107, 108 may be combined with spring element 163 for detecting of pH and redox potential for a sample 13, 113, 173 of monitored media placed on or in close proximity to the surfaces of the spring elements.

Figure 7:
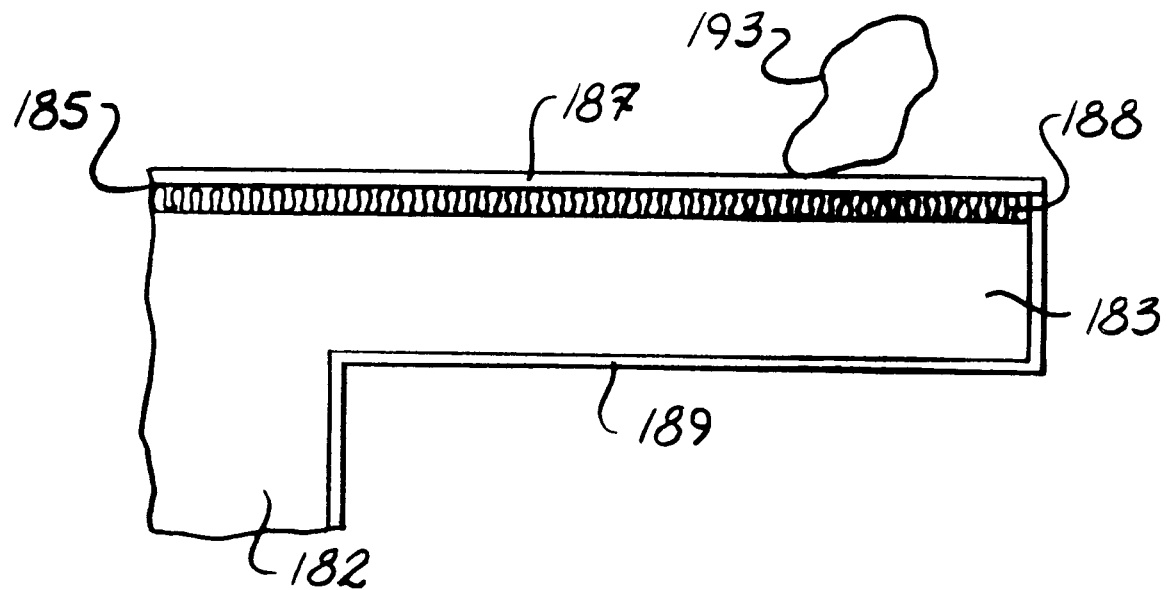
FIG. 7 is a cross-sectional side view of an alternate embodiment of the microcantilever of the present invention with an ion selective membrane and an insulator coating.

Another detection and monitoring method utilizes the microcantilevered spring element 183 of FIG. 7 to detect and measure selective ion concentrations of a sample 193 of monitored media placed on the coated regions of the spring element. As shown in FIG. 7, the spring element 183 is attached to base 182, with a first surface 185 having two coatings. The outer coating 187 on the first surface is composed of a ion selective membrane such as a biopolymer or a protein in a uniform layer 187. The outer coating 187 allows potassium, calcium, sodium, lithium, calcium, magnesium, cesium, ammonium, chloride, flouride, sulfide, both cations and anions, or other ions to pass from the sample 193 through the coating 187. The ion-selective membrane coating 187 may comprise polyvinyl chloride material containing potassium, calcium, potassium ionophore valinomycin, or other polyvinyl chloride material that selectively passes ions through the material. Such ion-selective membranes are well known in the art in theory and operation. (See *Ion-Selective Electrodes in Analytical Chemistry*, Vol. 1, edited by Henry Freiser, Plenum Press, New York (1978), pages 270–281.)

For selective sodium ion passage, a sodium ionophore valinonycin membrane material is placed in the outer coating 187. The ions pass through the outer coating and react with the chemical which has been coated on the inner coated region 188 underneath the outer coating 187. The detection capabilites of the outer coating 187 are insulated from the properties of the base 182 or the spring element 183 due to a second layer of active insulator 188 which is a chemical coating between the outer coating 187 and the base 182 and the spring element 183. The active insulator 188 may consist of silicon oxide, silicon nitride, aluminum oxide, iridium oxide, tantalum pentoxide and silicon or other polymers which are insulators to the passage of ions.

Figure 8:
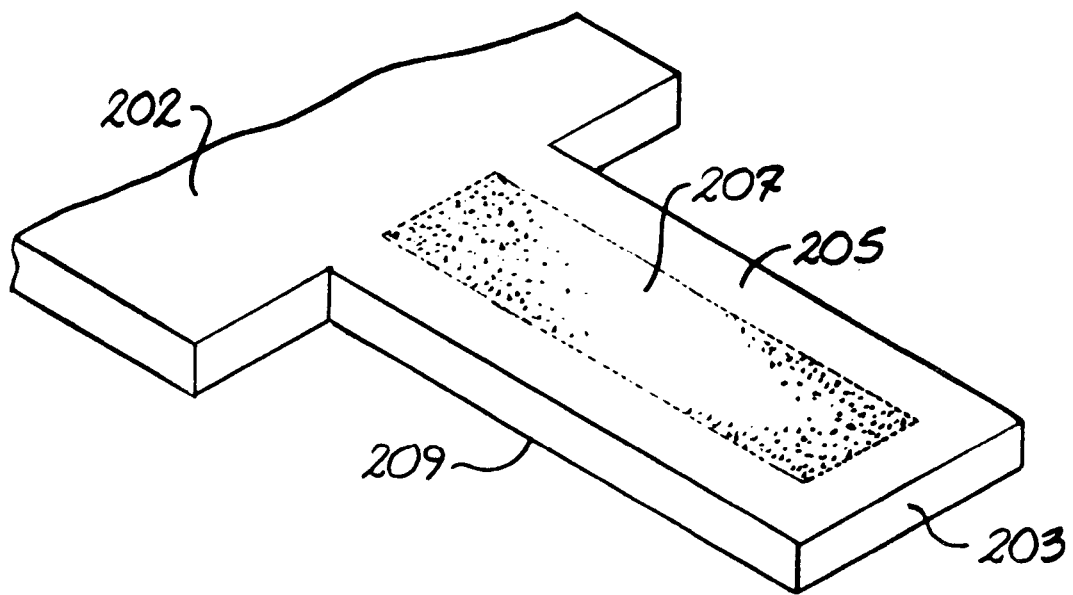
FIG. 8 is a side perspective view of another alternate embodiment of the microcantilever of the present invention with a coated region within an enclosing insulating region of a differing coating.
Figure 12:
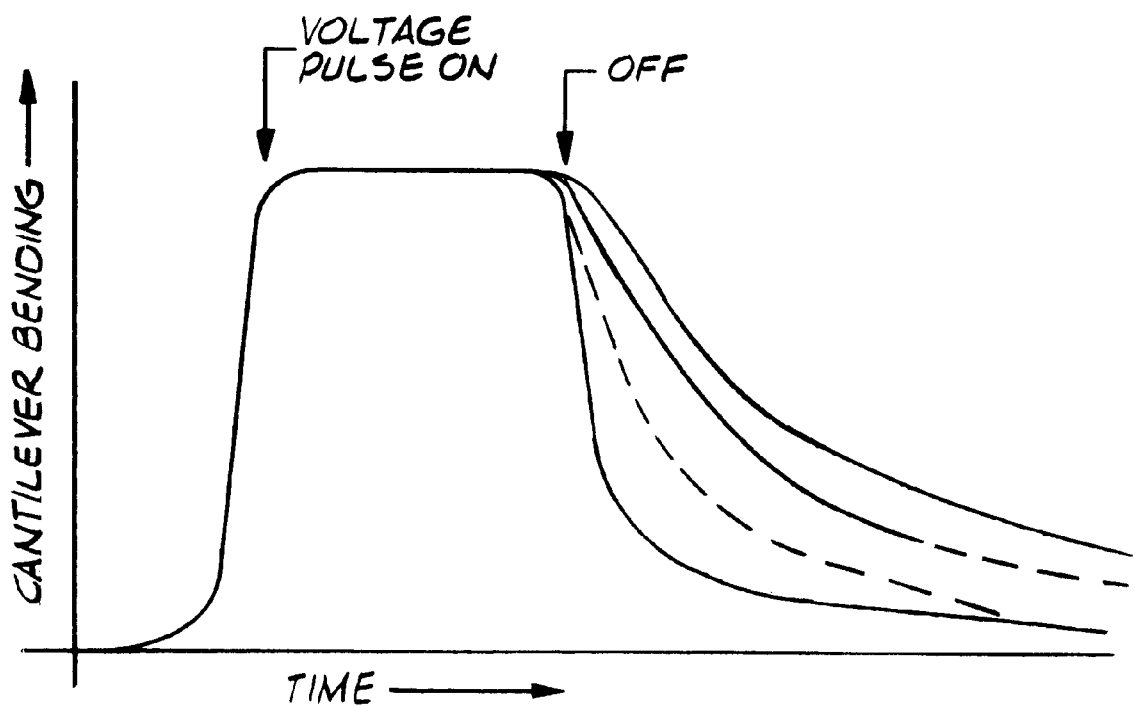
FIG. 12 is a graph which illustrates the microcantilever response to a application of a periodic electrical charge.
Figure 13:
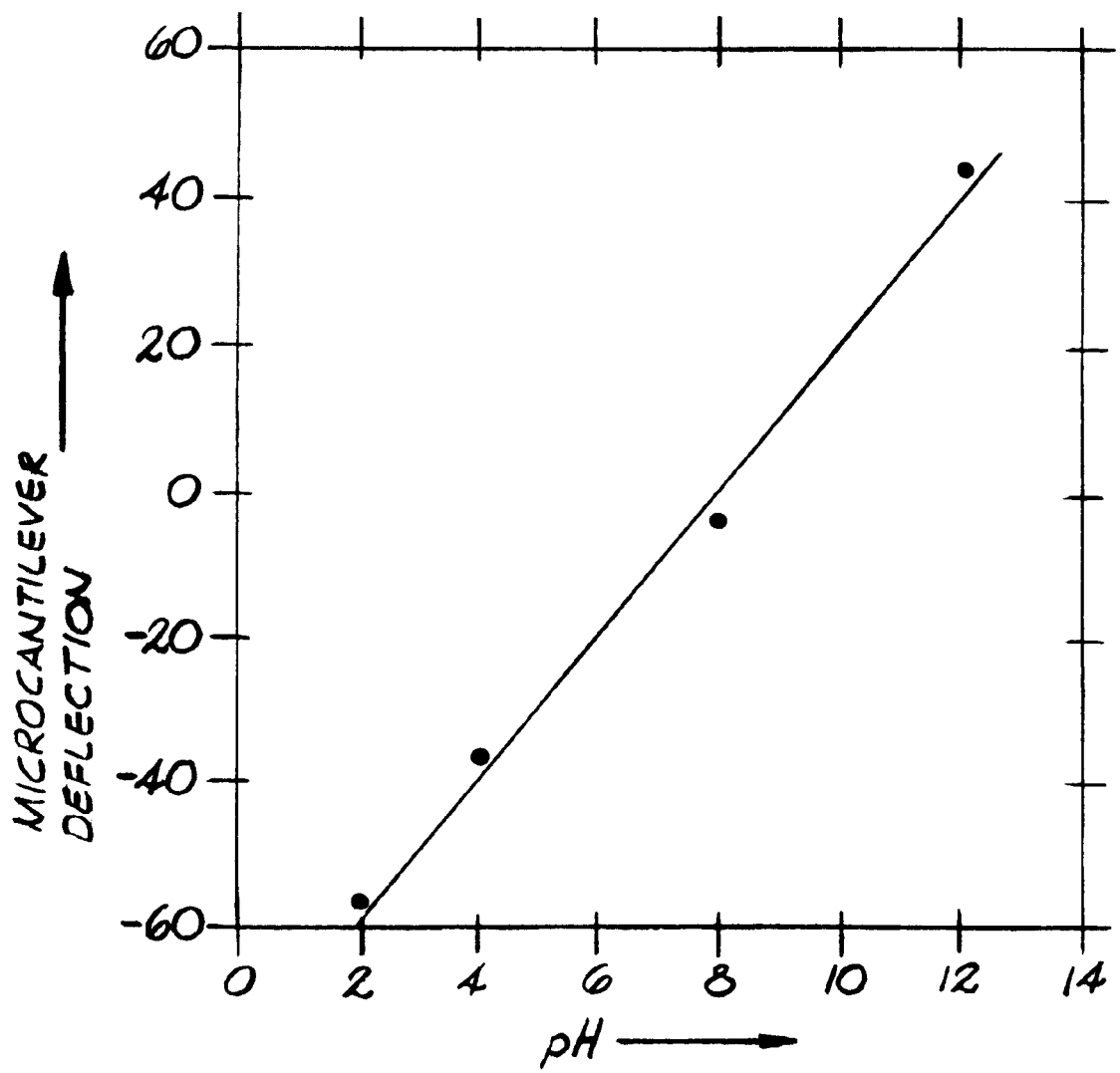
FIG. 13 is a graph which illustrates microcantilever response pH changes in a sample of monitored media.

Another detection and monitoring method utilizes the microcantilevered spring element 203 of FIGS. 8 and 9 to detect and measure changes and rates of changes of pH, redox potential, and specific ion concentrations in a sample 213 of monitored media by providing periodic electrical charges to least one microcantilevered spring element 203. With voltage pulsed from a controlling electrode 217 (FIG. 9), to an ohmic contact 215 attached to the transducer base 202 where the cantilever is made of semiconductors or insulated conductors. As depicted in FIG. 9, the spring element 203 is periodically charged to a steady state bending. The removal of a charge allows the spring element to rebound to a neutral position (FIG. 8). The time response of the decay curve (FIG. 12) will vary depending on mechanical stresses imposed on the coated surface 205 in relation to the surface 209 having an inert material, as the sensing chemical 207 reacts with the pH, redox potential, and specific ion concentrations exposed to the appropriate chemical coating 207 on surface 205 of the spring element 203.

A plurality of microcantilevered spring elements 3 can be made into an array (not shown) of a plurality of microcantilevers, each having differing coatings which react to biomaterials, hydrogen ions, redox potential, and/or selective ion concentrations in a sample of media. Deflections due to mechanical stresses of the surfaces of each of the plurality of spring elements may be calibrated by amplifying 120 the raw detector data, processing the detector data through an integrated microprocessor 121 utilizing preprogrammed analysis. Reference cantilevers can be used to eliminate the effects of temperature, viscocity, and pressure changes on the plurality of sensing microcantilevered spring elements. Reference cantilevers can also be used for eliminating the effects of liquid flow rate across the sensing cantilevers.

The volume of solution needed for detection of any of the embodiments may be as small as a nanoliter of sample, or less than 30 microliter of a sample 13 of media placed on the sensing surface. The value can range from nanoliters placed on the cantilever surface, to many cc of liquid, where the cantilever is placed in the liquid media to be monitored. Therefore the microcantilevered spring element 3, 103, 123, 143, 163, 183, and 123 with sensing coatings 7 may detect and measure biophysical and biochemical parameters in a sample of media, representing a breakthrough in the development of sensitive biochemical microsensors.

Unique features of the detection apparatus and method of utilizing the transducer base 1 having an attached microcantilevered spring element 3 includes: extremely sensitive and miniaturized; ideal for small volumes of media; additional microcantilevers can be used for detecting flow rate, pressure, and viscosity of media; broad ranges of a media's parameters could be determined by a single cantilever; easily incorporated into other microcantilever sensor systems in an array design; utilizes battery power (for power to electronics); regenerates the alignment of the microcantilever when removed from the media to be sampled; rugged and portable; and the detection apparatus can be used with or without an electrochemical control for measurements in liquid media. An additional advantage of the sensor microcantilever 3 is its low power consumption and lack generation of localized electromagnetic fields. The dynamic range of the microcantilever 3 may be further increased by using several microcantilevers in an array (not shown).

Detection of Spring Element Deflections

Possible alternative detection means other than laser detection include measuring deflections by piezoresistive, piezoelectric, capacitive, and electron tunneling, all of which are conventionally known. Each detecting means determines changes in deflection of the microcantilevered spring element 3 with sensitivities comparable to the sub-nanometer sensitivity of the laser sensing means. A general discussion of deflection detection techniques utilized with microcalorimeters, and references for each alternative detection means is provided in Gimzewski et al. ("Observation of a chemical reaction using a micromechanical sensor," 217 Chem. Phys. Lett. 589, at 593 (1994)).

Method of Detecting and Measuring

Detecting and measuring hydrogen ions in a media with the present invention include the steps of: providing a transducer; attaching at least one microcantilever to the transducer; providing the microcantilever with a base having a material that is essentially inert, having a first surface and an opposing second surface; and providing a reflective area on a segment of a surface of the microcantilevered spring element 3.

On at least one surface of the microcantilever, a chemical is attached in a first coating onto a coated region, the chemical accumulates a surface charge in response to the physical or chemical parameters undergoing detection. For detection and measuring of hydrogen ions within a sample of media, a coating is selected which accumulates surface charges on the coated region due to the ionizing of components of the coating in response to hydrogen ions in the sample of media placed on or in close proximity to the coated region. A second coating of inert material may be distributed on the second surface of the microcantilever. Additionally, the base of the microcantilever may contain an inert material, providing an essentially inert material on which a lesser surface charge density develops upon exposing of the sample of media to the microcantilever's coated region. Due to the build-up of a surface charge density on one surface or one coated region of one surface, mechanical stresses are established within the coated region or along one surface of the microcantilever, and bending occurs.

Since localized variations in hydrogen ions and pH occurs near living organisms, the method of detecting can be utilized for detecting living biological organisms in a sample of media. The method and apparatus described above has the ability to accomodate a single cell on the coated region 7 of the microcantilevered spring element 3, with the cell's metabolic activities monitored by the proportional deflections of the microcantilevered spring element 3 created by interactions of the chemical coated on the coated region 7.

The method of detecting deflection of the cantilevered spring element is provided a detecting means, which may include: providing a photo-detecting means, which includes providing a laser light source with the source directing light at the reflective cantilever surface. The reflected light off of the cantilever surface is captured by positioning a light sensitive detector near the cantilever, the detector receiving reflected light from the cantilever surface before, during, and after bending of the microcantilever. The degree of bending is measured is reference to a neutral position of the cantilever, and a microprocessor is provided for analyzing deflection information from the measuring step. The changes in deflection are correlated with hydrogen ion concentrations within the monitored media by utilizing the microprocessor and mathematical formulas to calculate the hydrogen ion concentrations as a function of surface charge density and the degree of cantilever deflection when the cantilever's bending parameters are known.

The embodiments for detecting and measuring pH, redox potential, and/or selective ion concentrations in a sample placed on the spring element can also be used for detecting parameters of a gas stream by the accumulation of a surface charge density and associated spring element deflections in response to the detected and measured parameters in the gas stream.

Many variations will undoubtedly become apparent to one skilled in the art upon a reading of the above specification with reference to the figures. As the foregoing description is exemplary in nature, the spirit and scope of the invention should be limited only by the spirit and scope of the following appended claims.

What is claimed is:

1. An apparatus for detecting and measuring physical and chemical parameters in a sample of monitored media, comprising:
   a transducer base;
   at least one cantilevered spring element secured to said base, said spring element comprising:
     at least one surface having a coated region;
     at least one chemical attached on said coated region, wherein said at least one chemical accumulates a first surface charge in response to said parameters in said sample, said sample placed on or in close proximity to said coated region; and
     a second surface on said spring element having a surface charge different than said first surface charge; and
   a means for measuring a deflection of said spring element due to mechanical stresses established by said surface charge on said surface of said spring element.

2. The apparatus as described in claim 1, wherein said at least one chemical accumulates said surface charge in response to hydrogen ion concentrations in said sample of media placeable on or in close proximity to said coated region.

3. The apparatus as described in claim 2, wherein said at least one chemical is selected from the group consisting of silicon nitride, silicon oxide, iridium oxide, aluminum oxide, tantalum pentoxide, and pH sensitive polymers.

4. The apparatus as described in claim 1, wherein said at least one chemical accumulates said surface charge in response to a redox potential in said sample of media placeable on or in close proximity to said coated region.

5. The apparatus as described in claim 4, wherein said at least one chemical further comprises a layer of metal coated on said surface having a coated region, said metal selected from the group consisting of gold, platinum, and noble metals.

6. The apparatus as described in claim 5, wherein said at least one chemical further comprises an active insulator between said metal layer and said surface, said active insulator being selected from the group consisting of silicon oxide, silicon nitride, aluminum oxide, tantalum pentoxide, and iridium oxide.

7. The apparatus as described in claim 1, wherein said at least one chemical further comprises an ion selective membrane material, said membrane material coated on said at least one surface, said membrane material allowing ions from said sample to selectively pass through said membrane material to said coated region, where said surface charge accumulates in response to ions on said coated region.

8. The apparatus described in claim 7, wherein said coated region further comprises an active insulator between said membrane material and said at least one surface, said active insulator being selected from the group consisting of silicon oxide, silicon nitride, iridium oxide, aluminum oxide, and tantalum pentoxide.

9. The apparatus as described in claim 1, wherein said at least one cantilevered spring element further comprises at least one microcantilever, said microcantilever having a length of about 1 to about 200 $\mu$m, a width of about 1 to about 50 $\mu$m, and a thickness of about 0.3 to about 3.0 $\mu$m.

10. The apparatus as described by claim 1, wherein said at least one cantilevered spring element further comprises a cylindrical microcantilever having a length of about 1 to about 200 $\mu$m, and a diameter of about 1 to about 50 $\mu$m.

11. The apparatus as described by claim 10, wherein said cylindrical microcantilever comprises a tubular microcantilever having a wall thickness of about 0.3 to about 3.0 $\mu$m.

12. The apparatus as described in claim 1, wherein said at least one cantilevered spring element is composed of a material selected from the group consisting of ceramics, polymers, silicon oxide, silicon nitride, germanium, germanium dioxide, zinc oxide, gallium arsenide, and silicon compounds.

13. The apparatus as described in claim 1, wherein said deflection measuring means comprises:
a reflective region on said spring element;
a laser light source, said source positioned to direct light at said spring element;
a light sensitive detector, said detector positioned to receive reflected light from said cantilevered spring element; and
a microprocessor for determining the deflection of said cantilevered spring element.

14. The apparatus as described in claim 1, wherein said deflection measuring means further comprises one of a laser detection means, a piezoresistive detection means, a piezoelectric detection means, a capacitive detection means, and a electron tunneling detection means.

15. The apparatus as described by claim 1, wherein said at least one cantilevered spring element further comprises:
a plurality of cantilevered spring elements attached to said base, each of said spring elements comprising:
a surface having at least one coated region;
at least one chemical on said at least one coated region, said at least one chemical accumulates a first surface charge in response to said parameters in said sample, said sample placeable on or in close proximity to said at least one coated region; and
a second surface on each of said spring elements having a surface charge different than said first surface charge; and
a plurality of means for measuring deflections, each associated with a respective one of said plurality of cantilevered spring elements.

16. A method for detecting and measuring chemical and physical parameters in a sample of monitored media, comprising the steps of:
providing a transducer base comprising:
at least one cantilevered spring element attached to said base; and
at least one surface having a coated region on said spring element;
providing at least one material, said material accumulates a surface charge by ionizing in response to said parameters in said sample placeable on or in close proximity to said coated region;
coating said at least one material on said coated region;
exposing said at least one material to said sample, said sample placed on or in close proximity to said coated region;
providing a means for detecting a deflection of said cantilevered spring element due to mechanical stresses established by said surface charge on said at least one material on said surface of said spring element; and
detecting said deflection of said spring element.

17. The method as described in claim 16, wherein the step of providing a transducer base comprising at least one spring element further comprises providing a microcantilever, said microcantilever having a length of about 1 to about 200 $\mu$m, a width of about 1 to about 50 $\mu$m, and a thickness of about 0.3 to about 3.0 $\mu$m.

18. The method as described in claim 16, wherein the step of providing a transducer base comprising at least one spring element further comprises providing at least one cylindrical microcantilever having a length of about 1 to about 200 $\mu$m, and a diameter of about 1 to about 50 $\mu$m.

19. The method as described in claim 18, wherein said step of providing at least one cylindrical microcantilever further comprises providing a tubular microcantilever, said tubular microcantilever having a wall thickness of about 0.3 to about 3.0 $\mu$m.

20. The method as described in claim 16, wherein the step of providing a transducer base comprising at least one spring element further comprises providing said spring element composed of a material selected from the group consisting of ceramics, polymers, silicon nitride, germanium, germanium dioxide, zinc oxide, gallium arsenide, silicon oxide, and silicon compounds.

21. The method as described in claim 16, wherein the step of providing at least one material further comprises selecting said at least one material from the group consisting of silicon nitride, silicon oxide, iridium oxide, aluminum oxide, tantalum pentoxide, and pH sensitive polymers.

22. The method as described in claim 16, wherein the step of coating further comprises providing a layer of metal coated on said at least one surface having a coated region, said metal selected from the group consisting of gold, platinum, and noble metals.

23. The method as described in claim 22, wherein said step of coating further comprises coating an active insulator between said layer of metal and said at least one surface, said active insulator being selected from the group consisting of silicon oxide, silicon nitride, aluminum oxide, tantalum pentoxide, and iridium oxide.

24. The method as described in claim 16, wherein the step of coating further comprises coating an ion selective membrane on said at least one surface, said membrane selectively allowing ions to move through said membrane to said material on said coated region.

25. The method as described in claim 24, wherein said step of coating further comprises coating an active insulator between said membrane coating and said first surface, said active insulator being selected from the group consisting of silicon oxide, silicon nitride, aluminum oxide, tantalum pentoxide, and iridium oxide.

26. The method as described in claim 16, wherein the step of providing said deflection measuring means further comprises:

providing a reflective area on said spring element;

providing a laser light source, said source directing light at said reflective area;

positioning a light sensitive detector to receive light from said reflected area;

measuring reflected light from said reflective area;

providing a microprocessor for analyzing information from said positioning step and said measuring step;

estimating deflections of said spring element; and correlating said deflections of said spring element with said parameters within said sample.

27. The method as described in claim 16, wherein the step of providing said deflection measuring means further comprises selecting from the group consisting of a laser detection means, a piezoresistive detection means, a piezoelectric detection means, a capacitive detection means, and a electron tunneling detection means, said detection means determines changes in deflection of said cantilever.

28. An apparatus for detecting and measuring physical and chemical parameters in a sample of monitored media, comprising:

a transducer base;

a plurality of cantilevered spring elements attached to said base, each of said spring elements comprising:

a surface having at least one coated region;

at least one material on said at least one coated region, said material accumulates a first surface charge in response to said parameter in said sample placed on or in close proximity to said coated region; and a second surface on said spring element having a surface charge different than said first surface charge; and a plurality of means for detecting deflections of each of said spring elements due to mechanical stresses established by different surface charges on said spring element surfaces, each means for detecting deflections associated with a respective one of said spring elements.

29. The apparatus as described by claim 28, wherein said at least one material further comprises at least one chemical that accumulates said surface charge in response to hydrogen ions in said sample of media.

30. The apparatus as described by claim 28, wherein said at least one material further comprises at least one chemical that accumulates said surface charge in response to a redox potential in said sample of media.

31. The apparatus as described by claim 28, wherein said at least one material further comprises an ion selective membrane, said membrane coated on said surface, said membrane allowing ions from said sample to selectively pass through said membrane to said material on said coated region, where said surface charge accumulates in response to ions on said coated region.

32. The apparatus as described by claim 28, wherein each of said plurality of cantilevered spring elements comprises a microcantilever having a different length of about 1 to about 200 $\mu$m, a width of about 1 to about 50 $\mu$m, and a thickness of about 0.3 to about 3.0 $\mu$m.

\* \* \* \* \*